United States Patent
Reich et al.

(10) Patent No.: US 10,405,838 B2
(45) Date of Patent: Sep. 10, 2019

(54) SIDE-LOOKING LUNG BIOPSY DEVICE

(71) Applicant: KONINKLIJKE PHILIPS N.V., Eindhoven (NL)

(72) Inventors: Christian Reich, Eindhoven (NL); Bernardus Hendrikus Wilhelmus Hendriks, Eindhoven (NL); Waltherus Cornelis Jozef Bierhoff, Eindhoven (NL); Torre Michelle Bydlon, Eindhoven (NL); Vijay Parthasarathy, Andover, MA (US); Sven Stoffelen, Eindhoven (NL); Franciscus Marinus Antonius Maria Van Gaal, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/505,137

(22) PCT Filed: Aug. 28, 2015

(86) PCT No.: PCT/EP2015/069807
§ 371 (c)(1),
(2) Date: Feb. 20, 2017

(87) PCT Pub. No.: WO2016/030533
PCT Pub. Date: Mar. 3, 2016

(65) Prior Publication Data
US 2017/0273671 A1   Sep. 28, 2017

Related U.S. Application Data

(60) Provisional application No. 62/042,809, filed on Aug. 28, 2014.

(30) Foreign Application Priority Data

Oct. 3, 2014 (EP) .................................... 14187589

(51) Int. Cl.
*A61B 5/00* (2006.01)
*A61B 10/02* (2006.01)
(Continued)

(52) U.S. Cl.
CPC ........ *A61B 10/0275* (2013.01); *A61B 5/0075* (2013.01); *A61B 5/0084* (2013.01);
(Continued)

(58) Field of Classification Search
CPC . A61B 10/0275; A61B 10/0283; A61B 10/04; A61B 2010/045; A61B 5/14503;
(Continued)

(56) References Cited

U.S. PATENT DOCUMENTS 4,321,930 A * 3/1982 Jobsis .................. A61B 5/0059
600/344
5,349,954 A * 9/1994 Tiemann .............. A61B 5/0084
600/342
(Continued)

FOREIGN PATENT DOCUMENTS

EP        0910284 B1    1/2007
WO    199214399 A1    9/1992
(Continued)

OTHER PUBLICATIONS

Nachabe, R. et al "Estimation of Lipid and Water Concentrations in Scattering Media with Diffuse Optical Spectroscopy from 900 to 1600nm", Journal of Biomedical Optics, vol. 15, 037015, 2010.
(Continued)

*Primary Examiner* — Angela M Hoffa

(57) ABSTRACT

A biopsy device with a hollow shaft is suggested, the shaft having a wall and a distal end portion, wherein a sidewardly facing notch is formed in the distal end portion. At least two optical fibers are arranged in the wall of the shaft so that end surfaces of the fibers are arranged in a longitudinal direction at opposite positions with respect to the notch.

18 Claims, 5 Drawing Sheets

(51) Int. Cl.
  *A61B 5/06* (2006.01)
  *A61B 17/00* (2006.01)
  *A61B 90/00* (2016.01)
(52) U.S. Cl.
  CPC .......... *A61B 5/062* (2013.01); *A61B 10/0283* (2013.01); *A61B 2017/00057* (2013.01); *A61B 2090/3614* (2016.02)
(58) Field of Classification Search
  CPC .............. A61B 5/14507; A61B 5/1455; A61B 5/14551; A61B 5/14552; A61B 5/1459; A61B 5/0084; A61B 5/0086; A61B 5/0075; A61B 5/0059
  See application file for complete search history.

(56) References Cited

U.S. PATENT DOCUMENTS

| | | | | |
|---|---|---|---|---|
| 5,632,273 | A * | 5/1997 | Suzuki | A61B 5/0059 356/39 |
| 5,785,658 | A | 7/1998 | Benaron | |
| 6,716,222 | B2 | 4/2004 | McAlister | |
| 7,318,830 | B2 | 1/2008 | Mayoral | |
| 7,945,312 | B2 * | 5/2011 | Hular | A61B 5/0066 600/310 |
| 8,046,057 | B2 * | 10/2011 | Clarke | A61B 5/0066 600/129 |
| 8,162,824 | B2 * | 4/2012 | Vayser | A61B 1/00135 362/574 |
| 8,206,315 | B2 * | 6/2012 | Mark | A61B 10/0275 600/567 |
| 8,260,390 | B2 * | 9/2012 | Tang | A61B 5/0071 600/341 |
| 8,417,306 | B2 * | 4/2013 | Cheng | A61B 5/021 600/324 |
| 8,792,951 | B1 * | 7/2014 | Mao | A61B 5/7221 600/340 |
| 8,918,153 | B2 * | 12/2014 | Cheng | A61B 5/021 600/324 |
| 9,114,226 | B1 * | 8/2015 | Lash | A61M 29/00 |
| 9,179,985 | B2 * | 11/2015 | Hendriks | A61B 34/20 |
| 9,445,766 | B1 * | 9/2016 | Lash | A61M 29/00 |
| 9,468,379 | B2 | 10/2016 | Hendriks | |
| 9,693,729 | B1 * | 7/2017 | Lash | A61B 5/489 |
| 9,763,744 | B2 * | 9/2017 | Wilson | A61B 5/14556 |
| 9,775,587 | B2 * | 10/2017 | Bierhoff | A61B 10/0266 |
| 9,867,599 | B2 * | 1/2018 | Hendriks | A61B 10/04 |
| 2002/0010483 | A1 | 1/2002 | Follmer | |
| 2003/0093007 | A1 | 5/2003 | Wood | |
| 2005/0203419 | A1 * | 9/2005 | Ramanujam | A61B 5/0075 600/473 |
| 2007/0078500 | A1 * | 4/2007 | Ryan | A61B 5/0066 607/88 |
| 2007/0282404 | A1 * | 12/2007 | Cottrell | A61B 18/22 607/89 |
| 2008/0194969 | A1 * | 8/2008 | Werahera | A61B 5/0059 600/476 |
| 2008/0306391 | A1 * | 12/2008 | Hular | A61B 5/0066 600/478 |
| 2009/0221921 | A1 * | 9/2009 | Cottrell | A61B 18/22 600/478 |
| 2009/0326385 | A1 * | 12/2009 | Hendriks | A61B 5/0066 600/478 |
| 2010/0081964 | A1 * | 4/2010 | Mark | A61B 10/0275 600/566 |
| 2010/0280409 | A1 | 11/2010 | Mark | |
| 2010/0317964 | A1 * | 12/2010 | Hendriks | A61B 5/0075 600/424 |
| 2010/0331782 | A1 * | 12/2010 | Hendriks | A61B 5/0066 604/164.12 |
| 2011/0112388 | A1 * | 5/2011 | Kuech | A61B 5/14546 600/341 |
| 2011/0218445 | A1 * | 9/2011 | Braun | A61B 5/0084 600/478 |
| 2011/0251494 | A1 * | 10/2011 | Hendriks | A61B 5/0075 600/478 |
| 2011/0270093 | A1 * | 11/2011 | Desjardins | A61B 5/0075 600/476 |
| 2012/0116234 | A1 * | 5/2012 | Farcy | A61B 5/0071 600/478 |
| 2013/0267821 | A1 * | 10/2013 | Hashimshony | A61B 17/32056 600/407 |
| 2014/0228661 | A1 * | 8/2014 | Popa-Simil | A61B 10/0275 600/361 |
| 2015/0148629 | A1 * | 5/2015 | Wilson | A61B 10/0275 600/317 |
| 2015/0150459 | A1 * | 6/2015 | Werahera | A61B 5/0075 600/411 |
| 2015/0182206 | A1 * | 7/2015 | Hendriks | A61B 5/0073 600/429 |
| 2015/0265256 | A1 * | 9/2015 | Bierhoff | A61B 5/0075 600/427 |
| 2015/0297198 | A1 * | 10/2015 | Bierhoff | A61B 10/0266 600/429 |
| 2015/0351675 | A1 * | 12/2015 | Cheng | A61B 5/14552 600/323 |
| 2015/0359525 | A1 * | 12/2015 | Hendriks | A61B 5/6848 600/478 |
| 2016/0007841 | A1 * | 1/2016 | Wijbrans | A61B 5/6848 600/182 |
| 2016/0008057 | A1 * | 1/2016 | Peppou | A61B 5/6848 600/327 |
| 2016/0038076 | A1 * | 2/2016 | Muller | A61B 5/0084 600/306 |
| 2016/0151055 | A1 * | 6/2016 | Leblond | A61B 5/0073 600/317 |
| 2016/0338679 | A1 * | 11/2016 | Tehrani | A61B 5/0075 |
| 2016/0374563 | A1 * | 12/2016 | Hendriks | A61B 5/0075 600/478 |
| 2018/0055495 | A1 * | 3/2018 | Tehrani | A61B 5/0035 |

FOREIGN PATENT DOCUMENTS

| | | |
|---|---|---|
| WO | 199915079 A1 | 4/1999 |
| WO | 200042906 A2 | 7/2000 |
| WO | 2009109879 A2 | 9/2009 |
| WO | 2009115952 A1 | 9/2009 |
| WO | 2014068468 A1 | 5/2014 |
| WO | 2014132110 A1 | 9/2014 |
| WO | 2014162242 A1 | 10/2014 |
| WO | 2014162289 A1 | 10/2014 |
| WO | 2015121147 A1 | 8/2015 |

OTHER PUBLICATIONS

Farrel, T.J. et al "A Diffusion Theory Model of Spatially Resolved, Steady-State Diffuse Reflectance for the non-Invasive Determination of TIssue OPtical Properties", Med. Phys, vol. 19, pp. 879-888, 1992.

Nachabe, R. et al "Estimation of Biological Chromophores using Diffuse Optical Spectroscopy: Benefit of Extending the UV-VIS Wavelength Range to Include 1000 to 1600 nm", Optics Express, vol. 18, pp. 1432-1442, 2010.

Zhang, Q et al "Turbidity-Free Fluorescence Spectroscopy of Biological Tissue", Optics Letters, vol. 25, No. 19,. pp. 1451-1453, 2000.

Evers, D.J. et al "Diffuse Reflectance Spectroscopy: A New Guidance Tool for Improvement of Biopsy Procedures in Lung Malignancies.," Clinical Lung Cancer, vol. 13, No. 6, pp. 424-431, Apr. 2012.

* cited by examiner

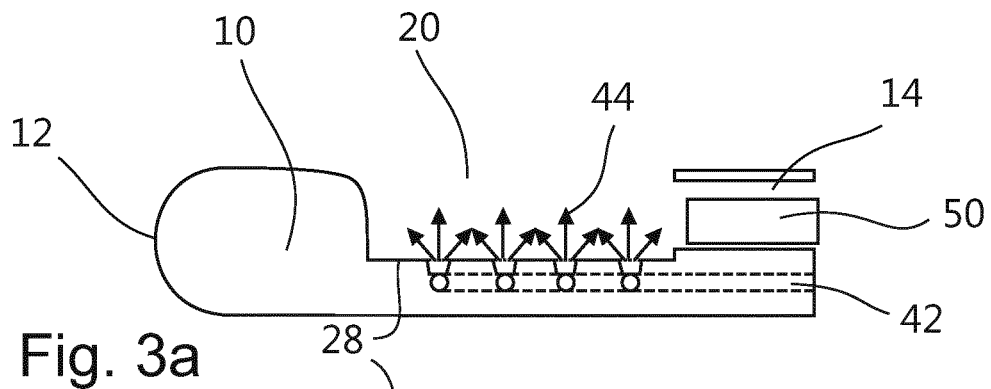
Fig. 3a
Fig. 3b
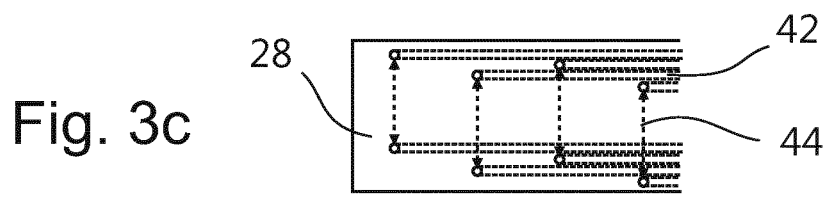
Fig. 3c
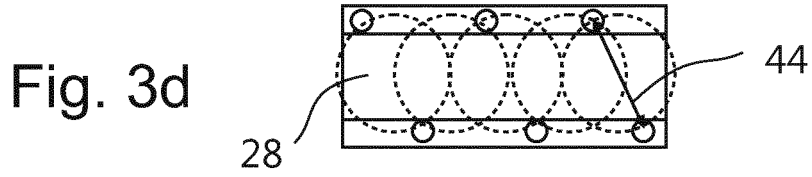
Fig. 3d
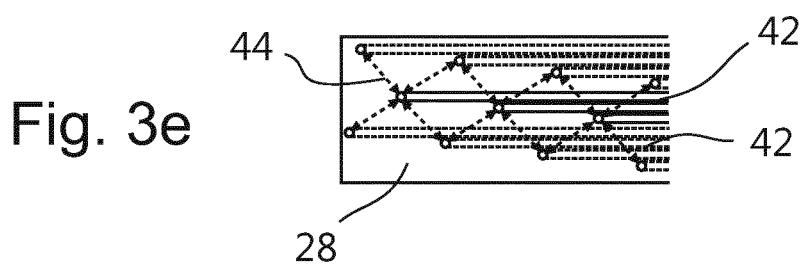
Fig. 3e

SIDE-LOOKING LUNG BIOPSY DEVICE

CROSS-REFERENCE TO PRIOR APPLICATIONS

This application is the U.S. National Phase application under 35 U.S.C. § 371 of International Application No. PCT/EP2015/069807, filed on Aug. 28, 2015, which claims the benefit of U.S. Provisional Patent Application No. 62/042,809, filed on Aug. 28, 2014 and European Patent Application No. 14187589.8, filed on Oct. 3, 2014. These applications are hereby incorporated by reference herein.

FIELD OF THE INVENTION

The invention generally relates to a system including a biopsy device with optical fibers and a lateral notch for in-vivo tissue inspection.

BACKGROUND OF THE INVENTION

For the early diagnosis of lung cancer, typically small biopsies are taken from the lung. Such biopsies can be obtained for instance through percutaneous insertions of a biopsy needle, or by introducing a bronchoscope into the airways of the lung (bronchi) with a biopsy tool via the working channel. For the latter, several types of biopsy tools can be used to obtain different kinds of tissue samples, such as forceps biopsies, needle aspiration biopsies, and brush biopsies for cytology. The sample should be of sufficient size to provide the pathologist with ample material for a proper evaluation.

Typical bronchoscopes are equipped with visual confirmation tools, allowing for inspection of the tissue sample prior to taking the biopsy. However, the size of such bronchoscopes with integrated optics does not allow for probing tissue from remote regions within the lung (small bronchi) with visual confirmation Such regions may be reached by protruding a smaller, flexible biopsy tool through the working channel of the bronchoscope, but the visual confirmation is not available any more. Further, the visual inspection can only confirm the presence of lesions which are visible on the surface of the bronchi. For the detection of tumors at an early stage, which typically originate behind the bronchi wall, the visual inspection is limited by the intrinsically superficial information. Further, the dimensions of the flexible tool will determine how deep the tool can be inserted into the bronchi, and should be therefore as compact as possible. For very small bronchi, it becomes important that the tool is capable of side-looking: Lesions behind the bronchi wall cannot be detected if the detection method is only forward directed, since there is no room left for positioning the front of the tool tip towards the suspected lesion.

As a result, potentially malignant lesions are often not noticed and/or the biopsy is taken at the wrong location resulting in false negatives. The number of biopsies should also be kept to a minimum, since every biopsy obtained has a risk of causing internal bleeding in the lung.

A way to add tissue sensing is by adding optical fibers to the flexible biopsy tools. An example is described in patent application EP 0910284 B1 where a forceps tool with in the center a fiber is integrated for tissue sensing based on optical spectroscopy. Studies have shown that lung tumors can be discriminated from normal lung parenchyma based on scattering and water content in the tissue. To determine these tissue parameters the fiber ends of the sending and receiving fiber should be sufficiently apart to reliably determine these parameters. Furthermore, to determine these parameters the probe must be able to sense the lung parenchyma beyond the bronchi wall. This means that the fiber ends must be at least 0.5 mm apart, more preferably 1 mm apart.

Other ways of adding optical fibers to a biopsy tool are disclosed in patent applications WO 2014/132110A1, WO 00/42906 A2 and WO 2014/068468 A1.

SUMMARY OF THE INVENTION

To overcome these limitations, novel concepts for a biopsy tool are needed and should include some or all of the following characteristics:

The tool should be capable of side-looking tissue characterization and tissue collection in the side way direction.

The tool should allow for 3D tissue characterization (up to some millimeters) to detect lesions behind the bronchi wall i.e. the optical fiber ends should be at least 0.5 mm apart, more preferably 1 mm apart from each other. In-depth tissue characterization (3D) can be achieved using diffuse reflectance spectroscopy. For this, optical light guides (fibers) can be incorporated into a bronchoscopic biopsy tool to provide tissue specific information on the target location prior to taking the biopsy.

The tool should allow for harvesting a tissue sample of sufficient size directly from the previously characterized location for pathological examination.

The tool may have a flexible tip, allowing for accessing very small bronchi.

Furthermore, the tool may have the ability to cauterize the tissue post-biopsy to prevent further bleeding.

The problem is how to add spectral tissue sensing to a small flexible biopsy tool, which allows for side-looking optical characterization of a tissue volume through the wall of small bronchi, before taking the biopsy at the same location.

According to the invention, a device is suggested providing an increased diagnostic yield from the target site. The invention proposes solutions for (i) lesion detection and location confirmation by spectral sensing and (ii) lateral sampling through the bronchi wall. This and further problems are solved by the subject-matter of the independent claim. Further embodiments are described in the dependent claims.

In general, optical fibers are incorporated into a biopsy device comprising a catheter with a flexible tip. The tip dimensions allow for accessing small bronchi (2 mm diameter, or less) and for obtaining a sufficiently large tissue sample to allow for pathological tissue classification. Two optical fibers are arranged in a way that the light path defined by the source and detection fibers will probe the same tissue volume which is also the target for the biopsy mechanism. At least one fiber end is located near the tip of the device. The fibers and the biopsy mechanism are integrated in a way to allow that a significant volume of the tissue is probed perpendicular to the longitudinal direction of the device, i.e. lateral to the device.

A system according to an embodiment may comprise a biopsy device with a hollow shaft, the shaft having a wall and a distal end portion, wherein a sidewardly facing notch is formed in the distal end portion. At least two optical fibers are arranged in the wall of the shaft so that end surfaces of the fibers are arranged in a longitudinal direction at opposite positions with respect to the notch.

A cutting element may be movably accommodated within the hollow shaft, wherein the cutting element may be formed as a cutting cone being movable inside the tool tip. Alternatively, the cutting element may be a small brush. This may allow for obtaining a tissue sample by scraping of tissue cells from the suspected lesion through movement and/or rotation of the brush within the exposed notch. This way of tissue sampling can minimize the risk of bleeding and yield sufficient tissue cells for cytological examination.

According to an embodiment, the end surface of at least one of the optical fibers is inclined relative to a longitudinal axis of the hollow shaft. By slanting the fiber end tip with a certain angle, the light output can be directed away from the fiber axis. For instance, the mismatch in refractive index at the slanted interface of a silica optical fiber and human lung tissue results in multiple (essentially two) beams which enter the tissue with different directions. This effect is dependent of the slanting angle.

According to an embodiment, a reflective layer may be provided at the inclined end surface of at least one of the optical fibers. It is noted that the reflective layer may be formed by reflective particles, wherein the reflective particles may be provided in a separately formed droplet or layer at the inclined surface of the tip of the fiber. Alternatively, an air bubble may be provided in front of the inclined fiber surface.

According to an embodiment, an additional optical fiber may be provided which is arranged in the shaft in such a way that an additional optical fiber and at least one of the optical fibers are optically coupled by the inclined end surface. That, light which is guided through an optical fiber and which is reflected by the inclined end surface is received by the additional fiber, or vice versa. Dependent on the inclination angle of the end surface, the light will be reflected with a predetermined angle. It will be understood that the orientation of the additional optical fiber should be in the direction of the reflected light to receive as much as possible of the reflected light.

According to an embodiment, the biopsy device may further comprise at least two additional optical fibers being arranged in the shaft so that end surfaces of the fibers are located in a lateral direction at opposite positions with respect to the notch. The plurality of optical fibers may be arranged in a regular pattern. For example, optical fibers may be arranged in or at the shaft such that two rows of end surfaces are arranged at the sides of the notch, respectively. Further examples will be described with reference to the drawings below.

According to an embodiment, the optical fibers of the biopsy device may include at least one source fiber for emitting light and at least one detector fiber for receiving light. The detector fibers and the source fibers may be arranged such that the space including tissue above or adjacent the notch can be observed.

According to an embodiment, the end surfaces of the optical fibers may be arranged outside the notch, i.e. in the walls (front, side and/or rear wall) of the shaft forming the notch. Alternatively and/or additionally, the end surfaces of the optical fibers may be arranged in the notch, i.e. in the bottom surface of the notch. For example, optical fibers can be included inside the tool for the purpose of allowing for characterization of the harvested tissue sample inside the notch. This would add additional confidence that the harvested tissue sample is indeed of diagnostic value.

According to an embodiment, the biopsy device may further comprise a channel for injecting or extracting a fluid, for example for injecting a drug or a contrast agent, or for extracting a sample of a body fluid. The integrated tube of the biopsy device may also be used for flushing and draining airways with liquid (aqueous solutions) for diagnostic purposes. The biopsy device may further comprise a suction device being adapted to apply vacuum to the channel.

According to an embodiment, the biopsy device may further comprise a console including a light source, a light detector and a processing unit for processing the signals provided by the light detector, the console being adapted for in-vivo tissue inspection. One of the light source and the light detector may provide wavelength selectivity. The light source may be one of a laser, a light-emitting diode or a filtered light source, and the console may further comprise one of a fiber switch, a beam splitter or a dichroic beam combiner. Furthermore, the device may be adapted to perform at least one out of the group consisting of diffuse reflectance spectroscopy, diffuse optical tomography, differential path length spectroscopy, and Raman spectroscopy.

According to an embodiment, the biopsy device may further comprise a means which enables electromagnetic tracking of the biopsy device. For example, the tip of the side-looking biopsy tool may be equipped with such a means, to allow for navigation of the tool within the lung. This offers the capability of controlled navigation of the biopsy tool beyond the visually accessible range of the bronchoscope and, at the same time, it also offers the on-the-spot tissue confirmation using spectral sensing as described herein. A means for electromagnetic tracking (EM-tracking) may be a coil or may be a LC-circuit including an inductor and a capacitor, wherein the inductor may be formed as a coil. The means for EM-tracking may be formed as a passive means which is configured to be activated by an external magnetic field, for example by a magnetic field of a MRI-system, so as to form a magnetic field in response to the activating magnetic field, which in turn may be sensed by the MRI-unit so that the means is traceable in MRI-images. Furthermore, the means, for example in form of an LC-circuit, may be made on a Si wafer. It is noted that a separate tip portion of the biopsy device may be made together with the means for EM-tracking on a Si wafer, wherein the separate tip portion may then be fixed to the shaft of the biopsy device.

According to an embodiment, the biopsy device may further comprise a radiopaque material at the distal end portion of the shaft for enhancing the visibility of that portion in a fluoroscopic image.

According to an embodiment, the distal end portion of the shaft of the biopsy device may be configured for cauterization immediately after a biopsy is taken. This would prevent the risk of excessive bleeding at the biopsy site which could be potentially fatal.

The biopsy device may also be designed in such a way that multiple biopsies can be taken and stored within a cannula without having to completely remove the probe from, for example, the airways before taking the next biopsy. A vacuum could be applied to suck the biopsy sample further into the cannula after cutting. With each new sample, the biopsy cores would be sucked further back into the cannula. Once all biopsies are acquired they can be removed after the probe is removed from the airways.

The aspects defined above and further aspects, features and advantages of the present invention may also be derived from the examples of embodiments to be described hereinafter and are explained with reference to examples of embodiments. The invention will be described in more detail hereinafter with reference to examples of embodiments but to which the invention is not limited.

BRIEF DESCRIPTION OF THE DRAWINGS

FIG. 3a is a side view and FIG. 3b a top view of a tip portion of a biopsy device according to a third embodiment. FIGS. 3c to 3e show exemplary pattern of end surfaces of optical fibers arranged at the notch.

The illustration in the drawings is schematically only and not to scale. It is noted that similar elements are provided with the same reference signs in different figures, if appropriate.

DETAILED DESCRIPTION OF EMBODIMENTS

Figure 1:
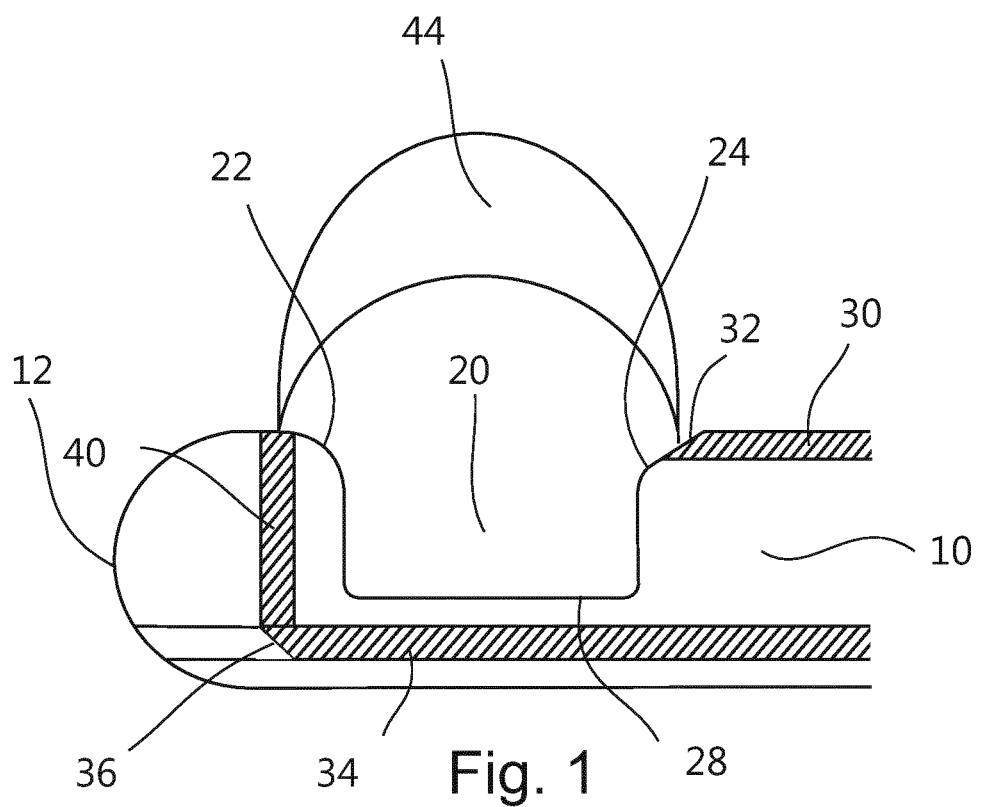
FIG. 1 is a side view of a tip portion of a biopsy device according to a first embodiment.

FIG. 1 shows a side view of a tip portion of a biopsy device according to a first embodiment comprising a shaft 10 with a sidewardly facing notch 20 and two optical fibers 30, 34. The tip portion of the shaft is formed with a blunt distal end 12, i.e. with rounded edges. The end of the shaft may have a part-spherical surface. Such a blunt end face of the shaft facilitates an introduction of the shaft through an existing path in a body, for example through bronchi into a lung, without harming the same. The notch comprises a front edge 22, a rear end 24 and a bottom 28, wherein the edges 22, 24 of the notch are rounded so that no sharp edge is at the tip portion of the shaft.

The first optical fiber 30 may have an end surface 32 which is cut with an inclined angle to the shaft axis. In a case in which the inclined end surface 32 of the first optical fiber 32 is arranged facing to the front but also to the side of and away from the shaft of the biopsy device, the refraction of emitted light will direct the light 44 sidewardly.

Figure 2:
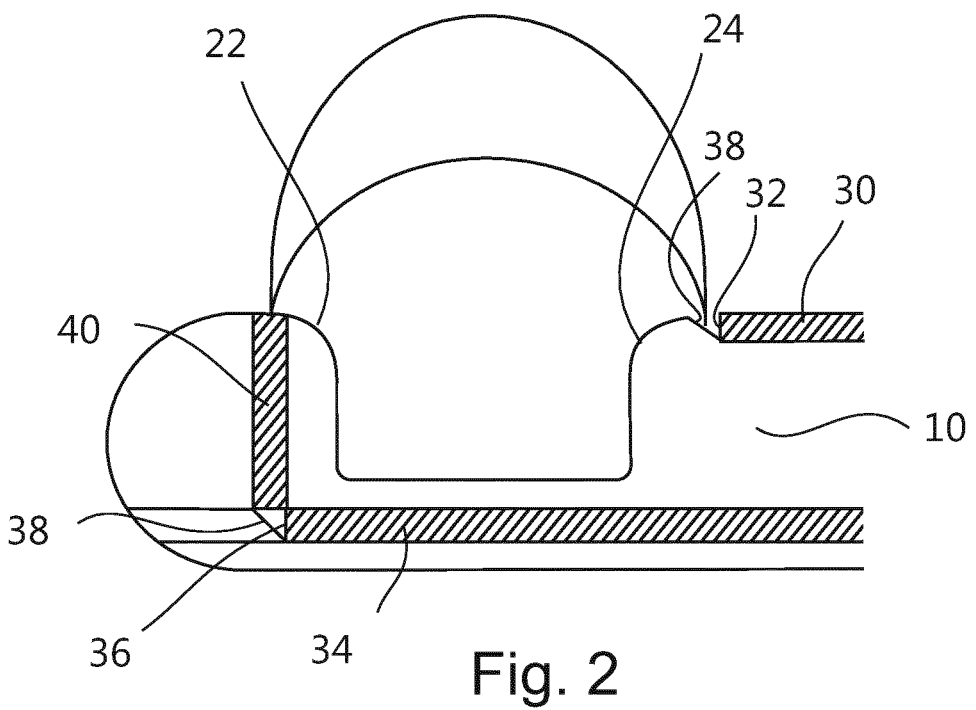
FIG. 2 is a side view of a tip portion of a biopsy device according to a second embodiment.

Otherwise, the first optical fiber 30 may have a straight cut end face, i.e. an end face which is cut perpendicular to the fiber axis, as shown in FIG. 2. The first optical fiber 30 may be integrated into the tip portion of the biopsy device so that the straight cut end face is facing a reflecting surface 38 (mirror) with a defined angle to direct the light 44 away from the fiber axis. For a perpendicular reflection, the tilt angle of the mirror should be 45°. The proposed mirror concept allows for directing the light output to the side relative to the shaft axis of the biopsy device using standard optical fibers.

In the embodiments of FIGS. 1 and 2, optical fibers 32, 34 are integrated in a way which allows for probing a tissue volume perpendicular to the axis of the tip (the tissue surrounding the tip). The fibers are preferably positioned at opposite positions with respect to the notch 20 of the tip portion. The light 44 is directed away from the axis of the biopsy device and into a tissue volume. As a consequence, the optical fibers are arranged for sensing along an optical path and within a volume that extend in a longitudinal direction of the shaft between end surfaces of the optical fibers. In other words, the optical fibers are arranged for sensing changes in the optical characteristics of a path between the end surfaces of the optical fibers that is longitudinal to direction of the shaft.

For the second optical fiber 34 positioned inside the tool tip, the light can be guided out of the tip along and through an additional optical fiber 40 which is integrated in a way that it collects the light which is redirected by a reflecting surface.

First of all, the tip of the second optical fiber 34 may comprise an end surface 36 which is inclined relative to the axis of the elongate shaft, so that the light emitted through the fiber will be directed in a desired direction, for example, perpendicular to the axis of the shaft. Air in front of the inclined end surface 36 of the second optical fiber 34 will cause an appropriate reflection of light at the inclined surface. This is exemplarily shown in FIG. 1.

To improve the reflection, an additional reflective layer 38 might be provided as the inclined surface in front of the straight cut end surface 36 of the second optical fiber 34, to improve the reflection of the emitted/received light to the desired direction. This is exemplarily shown in FIG. 2.

Alternatively, reflective particles might be provided in front of the tip of the fiber, wherein the reflective particles might be provided in a separately formed droplet or layer, to direct the light from the second optical fiber 34 to the additional fiber 40 or vice versa.

The void space (gap) between a reflecting surface 38 and a straight cut fiber tip end 32 of the first optical fiber 30 may be filled with a (quasi-) transparent glue (for visible and near-infrared wavelengths) which enhances the smoothness of the tip surface.

It is noted that additional scattering but non-absorbing particles with a refractive index different from the glue (such as titanium oxide, $TiO_2$) can be added to the glue mixture. For the collection fiber, this would have the advantage that more light from the illuminated tissue can be coupled into the fiber by scattering, and thereby improve the signal gain.

FIG. 3a shows a side view of a third embodiment of a biopsy device having a shaft 10, a notch 20, a channel 14 for accommodating a cutting element 50, as well as optical fibers 42 which are arranged in the shaft with the end faces located at the notch. It is noted, that a combination of features of the first, second and/or third embodiment may be advantageous. For example, the third embodiment may also comprise optical fibers 30, 34 as described in connection with the first and second embodiments above. Otherwise, the first and/or second embodiment may also comprise a channel 14 for accommodating a cutting element 50 or for suction.

As shown in the side view of FIG. 3a as well as the top view of this embodiment in FIG. 3b, the optical fibers 42 are arranged in a wall of the shaft 10 adjacent the lateral edges 26 of the notch, and along an axis of the biopsy device. The optical fibers 42 may be arranged within a boundary of the biopsy device, especially embedded in the lateral wall of the shaft 10. Each of the plurality of optical fibers 42 may be connected to a single optical port. Thus, one optical fiber can emit or receive a light signal from one spatially well-defined position in the notch 20.

As shown exemplarily in FIGS. 3c, 3d and 3e, pairs of optical source and detector fibers 42 may be positioned in a notch 20 to provide an even distribution of fibers allowing light 44 to be emitted into tissue and to be received from tissue. A pair of optical source and detector fibers may be positioned on a line perpendicular to an axis of the shaft 10, with subsequent pairs of optical source and detector fibers being positioned also with one common distance. The entire length of the notch 20 may be covered by evenly distributed optical fibers. Alternatively, the fibers may be geometrically distributed such that one source fiber forms a pair with two or more optical detector fibers, as shown in FIG. 3e.

Figure 4:
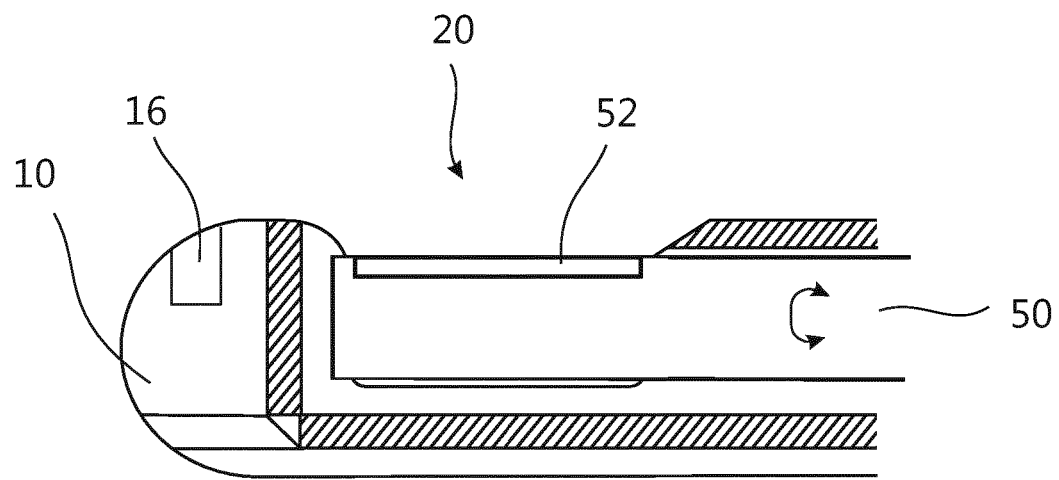
FIG. 4 is a side view of a tip portion of a biopsy device including a cutting element according to a first embodiment.

Referring to FIG. 4, the tip design allows for harvesting a tissue sample from essentially the same volume which is optically probed. A tissue biopsy can be secured in the notch 20 using a fully integrated, moveable cutting element 50. The cutting element itself may have a notch or recess 52 with sharp boundaries, which can be used for cutting a tissue sample by rotating the element, as indicated by the arrow in FIG. 4. During insertion of the tool towards the target location, the cutting element is in a "closed" position. At the target site, and after spectral tissue characterization, the cutting recess 52 can be moved into the "open" position, i.e. by rotation towards the notch 20 in the shaft 10, to allow for tissue to enter the recess 52. This can be assisted by applying underpressure, for instance via an empty syringe connected through a Luer-lock to the rear end of the cutting element 50. The tissue sample is obtained by rotating the cannula notch back into the "closed" position. Further shown in FIG. 4 is a means 16 which may be integrated into the tip portion of the biopsy device, the means allowing electromagnetic tracking of the tip portion. It will be understood that such a means may firstly be provided also at any other appropriate position of the tip portion and secondly may also be provided at any of the other embodiments disclosed herein.

Figure 5:
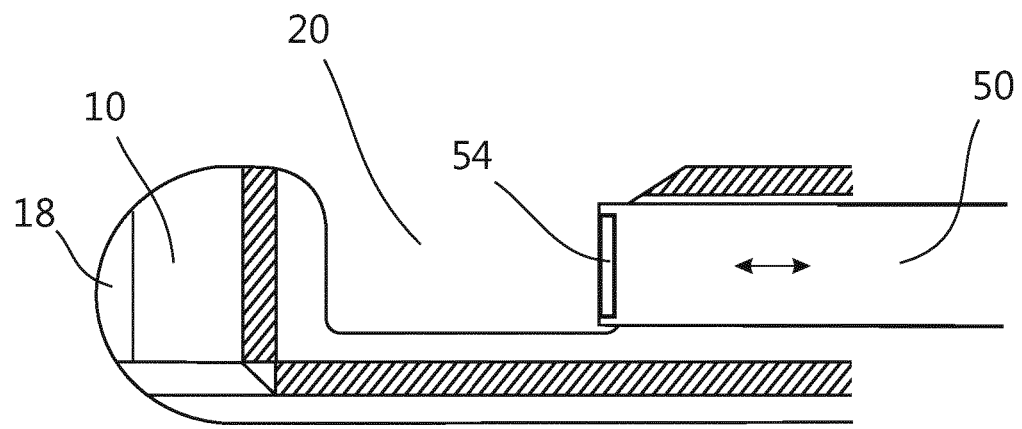
FIG. 5 is a side view of a tip portion of a biopsy device including a cutting element according to a second embodiment

Alternatively, as shown in FIG. 5, the cutting element 50 may have a recess 54 in the front surface and an edge between the front surface and a circumferential surface may be sharpened. Such a cutting element 50 may be push forwardly to cut a probe of tissue being in the notch 20 of the hollow shaft 10. Further shown in FIG. 5, as an example, is a portion 18 of the tip portion of the biopsy device, which portion 18 may be made from a radiopaque material so as to provide an enhanced visibility of the tip portion in a fluoroscopic image. It will be understood that such a material may firstly be provided also at any other appropriate position of the tip portion and secondly may also be provided at any of the other embodiments disclosed herein.

Figure 6:
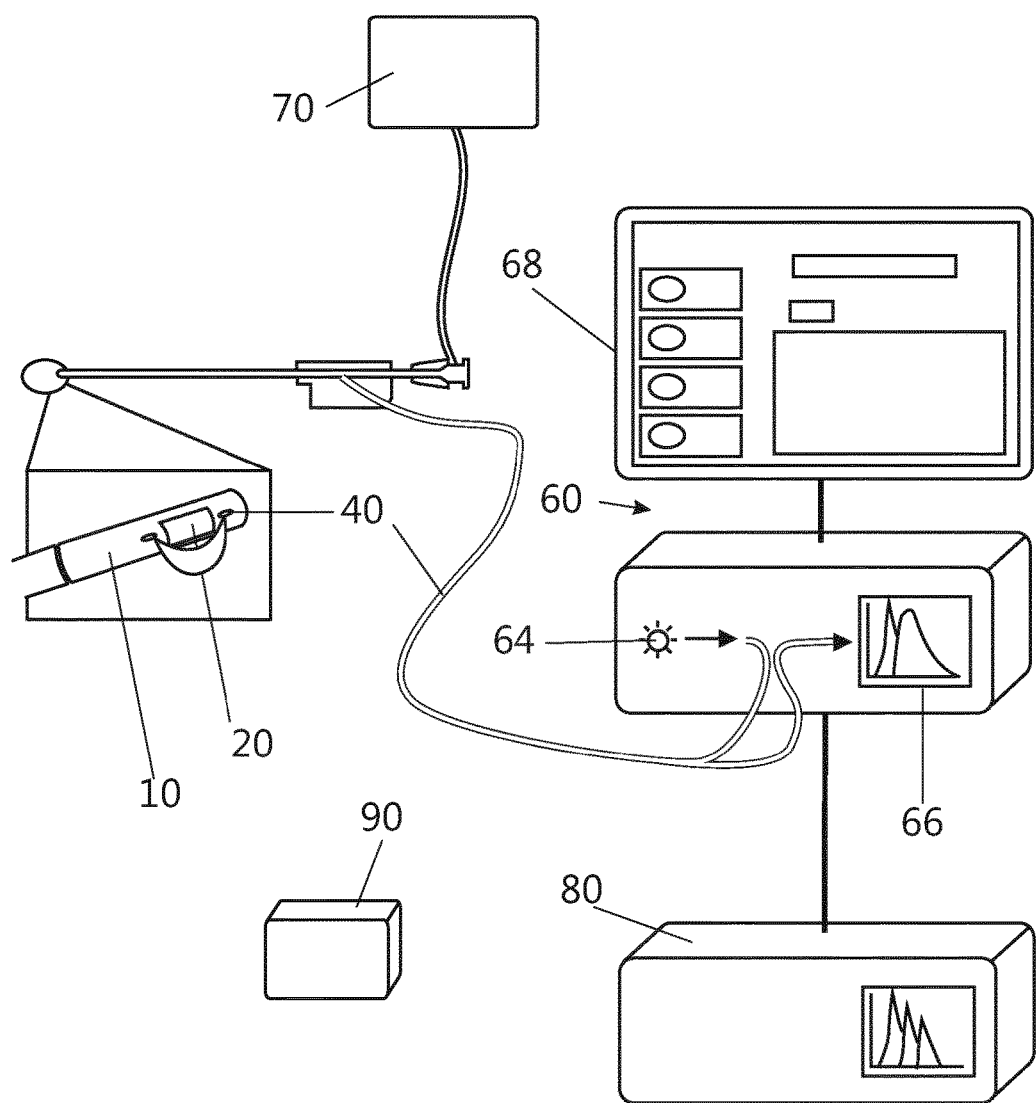
FIG. 6 shows a system including a biopsy device and a console.

As shown in FIG. 6, the fibers 40 of the interventional device are connected to an optical console 60. The optical fibers can be understood as light guides or optical waveguides. In an embodiment, the console 60 comprises a light source 64 in the form of a halogen broadband light source with an embedded shutter, and an optical detector 66. The optical detector 66 can resolve light with a wavelength substantially in the visible and infrared regions of the wavelength spectrum, such as from 400 nm to 1700 nm. The combination of light source 64 and detector 66 allows for diffuse reflectance measurements. For a detailed discussion on diffuse reflectance measurements see R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010).

Optionally it is also possible that the console is couple to an imaging modality capable of imaging the interior of the body, for instance when the biopsy is taken under image guidance. In this case it is also possible to store the image of the interior when the biopsy is taken to a container of the biopsy. In this case the in-vivo information of the optical biopsy needle, the information of the pathology of the biopsy as well as the location where the biopsy was taken are brought together for advanced pathology.

On the other hand, also other optical methods can be envisioned like diffuse optical tomography by employing a plurality of optical fibers, differential path length spectroscopy, fluorescence and Raman spectroscopy to extract tissue properties.

Further shown in FIG. 6 are a suction device 70, a device 80 for obtaining ex-vivo pathology information, and a storage container 90. The suction device may be connected to a proximal end of the biopsy device, such that underpressure or a vacuum can be applied through the biopsy device to the distal end of the same, in particular to the notch at the distal end of the biopsy device.

The device 80 may be connected to the console 60 by means of a wire or wireless, for interchanging information like control commands or data representing pathological aspects of an inspected tissue sample. The device 80 may be a digital pathology systems consisting of an optical scanner and an image management system to enable digitizing, storage, retrieval, and processing of tissue staining images, reading the information stored in the storage box container, and integrating this information with the digitized staining data set, to be presented to the pathologist. In addition to this, the data set from the photonic biopsy device may be either presented next to the histopathology image or the two data sets may be fused in the image, characterized and recognizable by a certain coloring pattern of the image. For instance the oxygenation level measured in-vivo could be added as a red color, where deep red means low oxygenation and bright red would mean high oxygenation level. Additionally, molecular spatial distributions from FTIR or Raman could be added as a color coded mapping to the pathology slide of specific molecules.

The tissue sample, which may firstly be subjected to an in-vivo tissue inspection, i.e. an inspection within a living body, and which may secondly subjected to an ex-vivo tissue inspection by means of the device 80, may be situated in the container 90. Molecular diagnostics can also be performed on the tissue biopsy (e.g. sequencing or PCR), or part of the biopsy The storage container for the biopsy may further be such that the optical information obtained in-vivo and/or ex-vivo can be stored on it. This can be a barcode label which can be read at the pathology department by the digital pathology device. It can also be a microchip where the optical information can be stored electronically. Instead of storing the actual information it is also possible to store an "address" or "link" of where the information may be retrieved.

According to another embodiment, the container 80 may be placed in the console 60. The data can then be written on the container while the photonic biopsy device is attached to the console. The data can be written in the form of a barcode or can electronically be stored in the chip on the container.

A processor transforms the measured spectrum into physiological parameters that are indicative for the tissue state and a monitor 68 may be used to visualize the results.

A computer program executable on the processor may be provided on a suitable medium such as an optical storage medium or a solid-state medium supplied together with or as part of the processor, but may also be distributed in other forms, such as via the Internet or other wired or wireless telecommunication systems.

For fluorescence measurements the console must be capable of providing excitation light to at least one source fiber while detecting tissue-generated fluorescence through one or more detection fibers. The excitation light source may be a laser (e.g. a semiconductor laser), a light-emitting diode (LED) or a filtered light source, such as a filtered mercury lamp. In general, the wavelengths emitted by the excitation light source are shorter than the range of wavelengths of the fluorescence that is to be detected. It is preferable to filter out the excitation light using a detection filter in order to avoid possible overload of the detector by the excitation light. A wavelength-selective detector, e.g. a spectrometer, is required when multiple fluorescent entities are present that need to be distinguished from each other.

In case fluorescence measurements are to be combined with diffuse reflectance measurements, the excitation light for measuring fluorescence may be provided to the same source fiber as the light for diffuse reflectance. This may be accomplished by, e.g., using a fiber switch, or a beam splitter or dichroic beam combiner with focusing optics. Alternatively, separate fibers may be used for providing fluorescence excitation light and light for diffuse reflectance measurements.

To perform spectroscopy, the acquired spectra may be fitted using a custom made Matlab 7.9.0 (Mathworks, Natick, Mass.) algorithm. In this algorithm, a widely accepted analytical model was implemented, namely the model introduced by the reference T. J. Farrel, M. S. Patterson and B. C. Wilson, "A diffusion theory model of spatially resolved, steady-state diffuse reflectance for the non-invasive determination of tissue optical properties", Med. Phys. 19 (1992) p. 879-888, which is hereby incorporated by reference in entirety. The input arguments for the model of this reference are the absorption coefficient $\mu_a(\lambda)$, the reduced scattering coefficient $\mu'_s(\lambda)$ and the center-to-center distance between the emitting and collecting fibers at the tip of the probe.

In the following part, the model will be explained briefly. The used formulas are mainly based on work of Nachabé et al., and reference is thus made to R. Nachabe, B. H. W. Hendriks, M. van der Voort, A. E., and H. J. C. M. Sterenborg "Estimation of biological chromophores using diffuse optical spectroscopy: benefit of extending the UV-VIS wavelength range to include 1000 to 1600 nm", Optics Express, vol. 18, 2010, pp. 1432-1442, which is hereby incorporated by reference in entirety, and furthermore reference is made to R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010), which is also hereby incorporated by reference in entirety.

A double power law function can be used to describe the wavelength dependence of the reduced scattering, where the wavelength $\lambda$ is expressed in nm and is normalized to a wavelength value of $\lambda_0=800$ nm. The parameter $\alpha$ corresponds to the reduced scattering amplitude at this specific wavelength.

$$\mu_s(\lambda) = \alpha\left(\rho_{MR}\left(\frac{\lambda}{\lambda 0}\right)^{-b} + (1-\rho_{MR})\left(\frac{\lambda}{\lambda 0}\right)^{-4}\right)[\text{cm}^{-1}] \quad \text{(Eq. 1)}$$

In this equation the reduced scattering coefficient is expressed as the sum of Mie and Rayleigh scattering where $\rho_{MR}$ is the Mie-to-total reduced scattering fraction. The reduced scattering slope of the Mie scattering is denoted b and is related to the particle size. For a homogeneous distribution of absorbers, the total light absorption coefficient $\mu_a(\lambda)$ can be computed as products of the extinction coefficients and volume fraction of the absorbers (see FIG. 8).

$$\mu_a^{Total} = f_1\mu_a^1 + f_2\mu_a^2 + f_3\mu_a^3 + \ldots \quad \text{(Eq. 2)}$$

Instead of modeling the absorption coefficient $\mu_a(\lambda)$ as the sum of absorption coefficients weighted by the respective concentrations of the four chromophores of interest, it was decided to express the tissue absorption coefficient as $$\mu_a^{Tissue}(\lambda) = C(\lambda)v_{Blood}\mu_a^{Blood}(\lambda) + v_{WL}\mu_a^{WL}(\lambda)[\text{cm}^{-1}] \quad \text{(Eq. 3)}$$

where $\mu_a^{Blood}(\lambda)$ corresponds to the absorption by blood and $\mu_a^{WL}(\lambda)$ corresponds to absorption by water and lipid together in the probed volume. The volume fraction of water and lipid is $v_{WL}=[\text{Lipid}]+[\text{H}_2\text{O}]$, whereas $v_{Blood}$ represents the blood volume fraction for a concentration of hemoglobin in whole blood of 150 mg/ml.

The factor C is a wavelength dependent correction factor that accounts for the effect of pigment packaging and alters for the shape of the absorption spectrum. This effect can be explained by the fact that blood in tissue is confined to a very small fraction of the overall volume, namely blood vessels. Red blood cells near the center of the vessel therefore absorb less light than those at the periphery. Effectively, when distributed homogeneously within the tissue, fewer red blood cells would produce the same absorption as the actual number of red blood cells distributed in discrete vessels. The correction factor can be described as $$C(\lambda) = \frac{1 - \exp(-2R\mu_a^{Blood}(\lambda))}{2R\mu_a^{Blood}(\lambda)} \quad \text{(Eq. 4)}$$

where R denotes the average vessel radius expressed in cm. The absorption coefficient related to blood is given by $$\mu_a^{Blood}(\lambda) = \alpha_{BL}\mu_a^{HbO_2}(\lambda) + (1-\alpha_{BL})\mu_a^{Hb}(\lambda)[\text{cm}^{-1}] \quad \text{(Eq. 5)}$$

where $\mu_a^{HbO_2}(\lambda)$ and $\mu_a^{Hb}(\lambda)$ represent the basic extinction coefficient spectra of oxygenated hemoglobin HbO$_2$ and deoxygenated hemoglobin Hb, respectively. The oxygenated hemoglobin fraction in the total amount of hemoglobin is noted $\alpha_{BL}=[\text{HbO}_2]/([\text{HbO}_2]+[\text{Hb}])$ and is commonly known as the blood oxygen saturation. The absorption due to the presence of water and lipid in the measured tissue is defined as $$\mu_a^{WL}(\lambda) = \alpha_{WL}\mu_a^{Lipid}(\lambda) + (1-\alpha_{WL})\mu_a^{H2O}(\lambda)[\text{cm}^{-1}] \quad \text{(Eq. 6)}$$

In this case the concentration of lipid related to the total concentration of lipid and water together can be written as $\alpha_{WF}=[\text{Lipid}]/([\text{Lipid}]+[\text{H}_2\text{O}])$, where [Lipid] and [H$_2$O] correspond to the concentration of lipid (density of 0.86 g/ml) and water, respectively.

This way of relating the water and lipid parameters in the expression of the absorption coefficient defined in Eq. 6, rather than estimating separately the water and lipid volume fraction corresponds to a minimization of the covariance of the basic functions for fitting resulting in a more stable fit cf. the reference R. Nachabe, B. H. W. Hendriks, M. van der Voort, A. E., and H. J. C. M. Sterenborg "Estimation of biological chromophores using diffuse optical spectroscopy: benefit of extending the UV-VIS wavelength range to include 1000 to 1600 nm", Optics Express, vol. 18, 2010, pp. 1432-1442. For further explanation and validation of this theorem reference is made to the reference R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010).

For example by means of the described algorithm optical tissue properties may be derived such as the scattering coefficient and absorption coefficient of different tissue chromophores: e.g. hemoglobin, oxygenated haemoglobin, water, fat etc. These properties are different between normal healthy tissue and diseased (cancerous) tissue.

Figure 8:
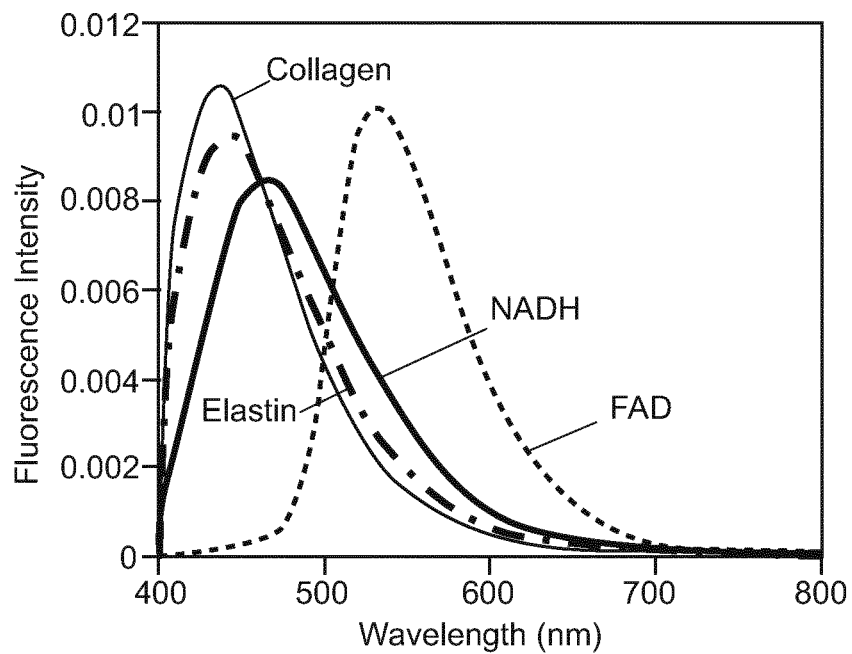
FIG. 8 shows fluorescence curves for collagen, elastin, NADH and FAD.

The main absorbing constituents in normal tissue dominating the absorption in the visible and near-infrared range are blood (i.e. hemoglobin), water and fat. In FIG. 8 the absorption coefficient of these chromophores as a function of the wavelength are presented. Note that blood dominates the absorption in the visible range, while water and fat dominate in the near infrared range.

Figure 7:
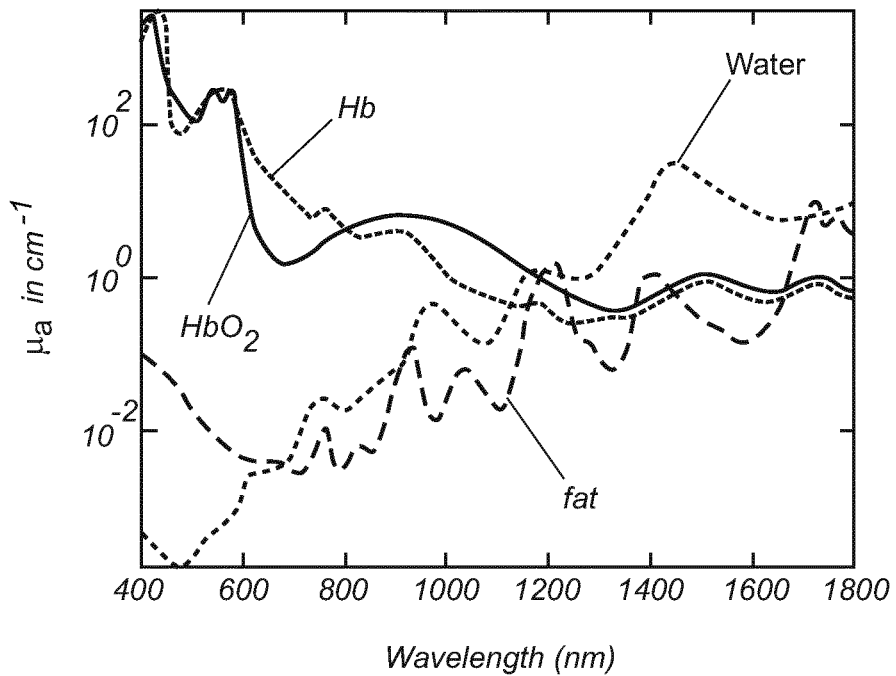
FIG. 7 shows a log plot of absorption coefficient of blood, water and fat.

The total absorption coefficient is a linear combination of the absorption coefficients of for instance blood, water and fat (hence for each component the value of that shown in FIG. 7 multiplied by its volume fraction). By fitting the model to the measurement while using the power law for scattering, the volume fractions of the blood, water and fat as well as the scattering coefficient may be determined.

Another way to discriminate differences in spectra is by making use of a principal components analysis. This method allows classification of differences in spectra and thus allows discrimination between tissues. Apart from diffuse reflectance also fluorescence may be measured. Then for instance parameters like collagen, elastin, NADH and FAD could be measured too (see FIG. 8). Especially, the ratio NADH/FAD, which is called the optical redox parameter, is of interest because it is an indicator for the metabolic state of the tissue, as described in Zhang Q., et al. "Turbidity-free fluorescence spectroscopy of biological tissue", Opt. Lett., 2000 25(19), p. 1451-1453, which is changed in cancer cells and assumed to change upon effective treatment of cancer cells.

It is also possible to detect the response of the body to exogenous fluorophores that can be detected by the optical biopsy device. Furthermore, these could also be linked to measurements of the exogenous fluorophores by imaging modalities like optical mammography based on diffuse optical imaging.

The described devices can be used in minimally invasive needle interventions such as low-back pain interventions or taking biopsies in the field of cancer diagnosis or in case where tissue characterization around the needle is required.

In the following, exemplary needle devices will be described with respect to their outer diameter, their insertion length, and their preferred use.

A biopsy needle might have an outer diameter of 1.27 mm up to 2.108 mm, might be inserted into tissue with 100 mm to 150 mm of its length, and might be used in soft tissue core biopsies in the neck, the head, the breast, the prostate, and the liver.

A fine aspiration needle of soft tissue might have an outer diameter between 0.711 mm and 2.108 mm, might be inserted into soft tissue with 100 mm to 150 mm of its length, and might be used for aspiration of soft tissue.

A brain biopsy needle might have an outer diameter of 2.108 mm, might be inserted into tissue with 150 mm up to 250 mm of its length, and might be used for diagnostic brain biopsies.

Finally, the device may include a needle electrode having an outer diameter of 2.108 mm and smaller, the electrode might be inserted into tissue up to 250 mm of its length, and might be used for radiofrequency ablation for instance of tumors.

While the invention has been illustrated and described in detail in the drawings and foregoing description, such illustration and description are to be considered illustrative or exemplary and not restrictive; the invention is not limited to the disclosed embodiments. Other variations to the disclosed embodiments may be understood and effected by those skilled in the art in practicing the claimed invention, from a study of the drawings, the disclosure, and the appended claims.

In the claims, the word "comprising" does not exclude other elements and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

LIST OF REFERENCE SIGNS 10 shaft
12 distal tip
14 channel
16 means for EM tracking
18 radiopaque material
20 notch
22 front edge
24 rear edge
26 lateral edge
28 bottom
30 first optical fiber
32 end surface
34 second optical fiber
36 end surface
38 reflecting layer
40 additional optical fiber
42 optical fiber
44 light path
50 cutting element
52 lateral recess
54 front recess
60 console
64 light source
66 light detector
68 monitor
70 suction device
80 device for ex-vivo tissue inspection
90 storage container

The invention claimed is:
1. A biopsy device comprising
a hollow shaft, the hollow shaft having a wall and a distal end portion, wherein a sidewardly facing notch is formed in the distal end portion,
at least two optical fibers arranged for sensing within a volume between and directly by respective end surfaces of the optical fibers, wherein the at least two optical fibers include at least one source fiber for emitting light and at least one detector fiber for receiving light, wherein the at least two optical fibers are arranged in the wall of the hollow shaft so that the respective end surfaces are arranged in a longitudinal direction of the hollow shaft at opposite positions with respect to the notch, wherein a distal end of a first one of the at least two optical fibers extends towards a distal end of a second one of the at least two optical fibers, and wherein the respective end surfaces of the at least two optical fibers are arranged outside the notch, and
a cutting device with a sharpened distal end or a brush movably accommodated within the hollow shaft and configured to obtain a tissue sample.

2. The biopsy device of claim 1, wherein the end surface of at least one of the at least two optical fibers is inclined relative to a longitudinal axis of the hollow shaft.

3. The biopsy device of claim 1, wherein the at least two optical fibers comprise an additional optical fiber arranged in the hollow shaft parallel to the longitudinal direction, wherein the additional optical fiber and the second one of the at least two optical fibers are optically coupled by a reflective layer.

4. The biopsy device of claim 1, wherein the at least two optical fibers comprise an additional optical fiber arranged in the hollow shaft parallel to the longitudinal direction, wherein the additional optical fiber and the second one of the at least two optical fibers are optically coupled by an inclined end surface of the additional optical fiber.

5. The biopsy device of claim 4, wherein an air gap extends in the wall and is present at the inclined end surface of the additional optical fiber.

6. The biopsy device of claim 1, further comprising at least two additional optical fibers being arranged in a lateral direction at opposite positions with respect to the notch.

7. The biopsy device of claim 6, wherein the at least two additional optical fibers includes at least four additional optical fibers that are evenly distributed along the notch.

8. The biopsy device of claim 1, wherein the biopsy device further comprises a channel for injecting or extracting a fluid.

9. The biopsy device of claim 1, further comprising a suction device configured to provide a vacuum, wherein the biopsy device further comprises a tissue retraction channel, wherein the suction device is coupled to the channel to apply vacuum to the channel.

10. The biopsy device of claim 1, further comprising a console including a light source, a light detector and a processor configured to process the signals provided by the light detector, the console being adapted for in-vivo tissue inspection.

11. The biopsy device of claim 1, further comprising a coil positioned on the distal end portion, distal of the notch and configured to enable electromagnetic tracking of the distal end portion.

12. The biopsy device of claim 11, further comprising a radiopaque material at the distal end portion of the hollow shaft.

13. The biopsy device of claim 12, wherein the distal end portion of the hollow shaft is configured for cauterization.

14. The biopsy device of claim 1, wherein the at least two optical fibers comprise an additional optical fiber arranged in the hollow shaft parallel to a longitudinal axis of the hollow shaft, wherein an end surface of the additional optical fiber is perpendicular relative to the longitudinal axis of the hollow shaft, the biopsy device comprising a reflective layer positioned within the wall between the second one of the at least two optical fibers and the additional optical fiber and configured to provide the optical coupling therebetween.

15. The biopsy device of claim 1, further comprising a vacuum, wherein the biopsy device further comprises a tissue retraction channel, wherein the vacuum is coupled to the channel to apply an underpressure to the channel.

16. A biopsy device comprising
a hollow shaft, the hollow shaft having a wall and a distal end portion, wherein a sidewardly facing notch is formed in the distal end portion,
at least two optical fibers arranged for sensing within a volume between and directly by respective end surfaces of the optical fibers, wherein the at least two optical fibers include at least one source fiber for emitting light and at least one detector fiber for receiving light, wherein the at least two optical fibers are arranged in the wall of the hollow shaft so that the respective end surfaces are arranged in a longitudinal direction of the hollow shaft at opposite positions with respect to the notch, wherein a distal end of a first one of the at least two optical fibers extends towards a distal end of a second one of the at least two optical fibers, and wherein the respective end surfaces of the at least two optical fibers are arranged outside the notch, and
a cutting device movably accommodated within the hollow shaft and configured to obtain a tissue sample.

17. The biopsy device of claim 16, further comprising a vacuum, wherein the biopsy device further comprises a tissue retraction channel, wherein the vacuum is coupled to the channel to apply an underpressure to the channel.

18. The biopsy device of claim 16, further comprising a suction device configured to provide a vacuum, wherein the biopsy device further comprises a tissue retraction channel, wherein the suction device is coupled to the channel to apply vacuum to the channel.

* * * * *